(12) United States Patent
Knight et al.

(10) Patent No.: US 9,861,100 B2
(45) Date of Patent: Jan. 9, 2018

(54) AGROCHEMICAL OIL BASED CONCENTRATES

(71) Applicant: CRODA INTERNATIONAL PLC, Yorkshire (GB)

(72) Inventors: Kathryn Marie Knight, Yorkshire (GB); James Alexander Flavell, Yorkshire (GB)

(73) Assignee: CRODA INTERNATIONAL PLC, East Yorkshire (GB)

( * ) Notice: Subject to any disclaimer, the term of this patent is extended or adjusted under 35 U.S.C. 154(b) by 9 days.

(21) Appl. No.: 15/127,997

(22) PCT Filed: Mar. 5, 2015

(86) PCT No.: PCT/GB2015/050636
§ 371 (c)(1),
(2) Date: Sep. 21, 2016

(87) PCT Pub. No.: WO2015/145105
PCT Pub. Date: Oct. 1, 2015

(65) Prior Publication Data
US 2017/0105411 A1   Apr. 20, 2017

(30) Foreign Application Priority Data
Mar. 25, 2014 (GB) .................................. 1405271.6

(51) Int. Cl.
| | | |
|---|---|---|
| A01N 25/30 | (2006.01) | |
| A01N 25/02 | (2006.01) | |
| A01N 59/20 | (2006.01) | |
| A01N 59/16 | (2006.01) | |

(52) U.S. Cl.
CPC ............. *A01N 25/30* (2013.01); *A01N 25/02* (2013.01); *A01N 59/16* (2013.01); *A01N 59/20* (2013.01)

(58) Field of Classification Search
None
See application file for complete search history.

(56) References Cited

U.S. PATENT DOCUMENTS

| | | | |
|---|---|---|---|
| 2,662,068 A | 12/1953 | Floyd | |
| 6,726,999 B2 * | 4/2004 | Schueler | C08L 67/02 428/474.9 |
| 2004/0157745 A1 | 8/2004 | Vermeer et al. | |
| 2005/0032647 A1 | 2/2005 | Deckwer et al. | |
| 2005/0233906 A1 | 10/2005 | Schnabel et al. | |
| 2010/0144527 A1 | 6/2010 | Patel et al. | |
| 2010/0190648 A1 * | 7/2010 | Tollington | A01N 25/04 504/234 |
| 2012/0208700 A1 | 8/2012 | Hopkins et al. | |

FOREIGN PATENT DOCUMENTS

| | | |
|---|---|---|
| EP | 0939782 | 9/1999 |
| EP | 1453885 | 9/2004 |
| EP | 1571908 | 9/2005 |
| WO | 9817705 | 4/1998 |
| WO | 0018227 | 4/2000 |
| WO | 0040216 | 7/2000 |
| WO | 02092663 | 11/2002 |
| WO | 2004083280 | 9/2004 |
| WO | 2007135384 | 11/2007 |
| WO | 2008141777 | 11/2008 |
| WO | 2010127408 | 11/2010 |
| WO | 2011070051 | 6/2011 |

OTHER PUBLICATIONS

English language International Search Report for PCT/GB2015/050636, dated Apr. 16, 2015, 4 pages.
"Performance additives for waterborne and solventborne systems Innovation @BULLET Compliance @BULLETHigh performance", Feb. 28, 2013 (Feb. 3, 2013) retrieved from the internet: URL:http://www.altenpflege-online.net/img/navigato/lack/multimedia/ELEMENTIS_MM_DOC Rheolate150.pdf, retrieved on Apr. 15, 2015, p. 24.

* cited by examiner

*Primary Examiner* — Johann R Richter
*Assistant Examiner* — Danielle Sullivan
(74) *Attorney, Agent, or Firm* — RatnerPrestia

(57) ABSTRACT

Structurants for agrochemical oil based active formulations, and in particular for use in agrochemical concentrate and diluted concentrates, for suspending solids in oil based formulations. The solids are one or more agrochemical actives and/or nutrients which are dispersed in the formulations. The structurant is polyamide formed from a dicarboxylic acid comprised from a dimer acid compound, and one or more diamine compounds. The present invention also includes methods of treating crops with such micronutrient formulations.

16 Claims, No Drawings

AGROCHEMICAL OIL BASED CONCENTRATES

CROSS REFERENCE TO RELATED APPLICATIONS

This application is the National Stage filing of International Appln. No. PCT/GB2015/050636, filed 5 Mar. 2015, and claims priority of GB Application No. 1405271.6, filed Mar. 25 2014, the entirety of which applications is incorporated herein by reference for all purposes.

The present invention relates to structurants for agrochemical oil based active formulations, and in particular for use in said formulations for suspending solids in oil based concentrate type formulations comprising one or more agrochemical actives and/or nutrients dispersed therein. The present invention also includes methods of treating crops with such formulations.

Oil based agrochemical concentrates are used for agrochemical actives that are insoluble in the oil (and usually also insoluble in water or other commonly used solvents). Such oil based systems typically incorporate the agrochemical active as a dispersion of solid particles in the oil which may include surfactants to facilitate emulsion formation on dilution in water for spraying and/or to improve the dispersion of the solid active in the oil.

When the agrochemical active ingredient is insoluble or only partly soluble in oil, the concentrate comprising the active is conveniently supplied in the form of a dispersion in which finely divided solid particles of agrochemical are suspended in an oil formulation. These concentrates are referred to as oil dispersions (OD) formulations, but are also known as oil flowable, oil concentrate, oil suspension concentrate, and non-aqueous suspension concentrate formulations. In OD formulations, it is desirable to reduce the tendency of the solid active to separate from the oil, particularly arising from density differences between active and oil. One way of reducing separation is to include a structurant in the oil phase. The structure in the oil phase typically helps improve physical stability of the formulation.

Current methods of providing structure in OD formulations include the use of synthetic or natural clays, for example Englehard's Attagel 50 (an attapulgite clay), and organic materials typically based on castor oil or derivatives of castor oil, e.g. as described in US 2005/233906 and EP 1571908. However, using such structurants has the disadvantage that the inclusion of surfactants, particularly anionic surfactants, tends to break down the structuring and reduce the stability of the dispersion.

It is important that the solid particles remain dispersed in the concentrate formulation without significant separation over an extended period of time under typical storage conditions. It is also important to prevent the dispersed solid particles in the concentrate from settling or forming a hard pack sediment upon storage.

Therefore, there is a need for structurants for agrochemical applications which are able to structure oil based concentrates. Additionally, there is a need for structurants which are able to keep solid particles dispersed in oil-based dispersions without negatively impacting the finished product viscosity, and which are able to maintain solid active ingredient in dispersion for a period of time to allow for storage without breakdown of the dispersion.

The present invention also seeks to provide the use of structurants in agrochemical concentrate compositions in combination with an agrochemical active, where the structurant may provide comparable or improved properties compared to existing structurants.

The present invention also seeks to provide the use of agrochemical concentrates and dilute formulations thereof comprising said structurants.

According to a first aspect of the present invention there is provided an agrochemical concentrate comprising;
i) an oil system comprising an oil and at least one structurant, said structurant being polyamide formed from a dicarboxylic acid comprised from a dimer acid compound, and one or more diamine compounds;
ii) at least one agrochemical active and/or nutrient dispersed in said oil system.

According to a second aspect of the present invention there is provided a method of preparing a concentrate according to the first aspect, said method comprising mixing;
at least one structurant, said structurant being polyamide formed from a dicarboxylic acid comprised from a dimer acid compound, and one or more diamine compounds, and an oil to form an oil system; and
at least one agrochemical active and/or nutrient.

According to a third aspect of the present invention there is provided an agrochemical formulation formed by dilution of the concentrate according to the first aspect or the second aspect.

According to a fourth aspect of the present invention there is provided the use of polyamide formed from a dicarboxylic acid comprised from a dimer acid compound, and one or more diamine compounds, as a structurant in an agrochemical concentrate comprising oil and at least one agrochemical active and/or nutrient.

According to a fifth aspect of the present invention there is provided a method of treating vegetation to control pests, the method comprising applying an agrochemical formulation of the third aspect, either to said vegetation or to the immediate environment of said vegetation.

It has been found that polyamide formed from a dicarboxylic acid comprised from a dimer acid compound, and one or more diamine compounds provides for structurants having good oil structuring properties, and which can allow for formation of physically stable dispersions of agrochemical actives.

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, when describing the number of carbon atoms in a substituent group (e.g. '$C_1$ to $C_6$ alkyl'), the number refers to the total number of carbon atoms present in the substituent group, including any present in any branched groups. Additionally, when describing the number of carbon atoms in, for example fatty acids, this refers to the total number of carbon atoms including the one at the carboxylic acid, and any present in any branch groups.

The term 'structurant' refers to the provision of effects ranging from increasing the viscosity (viscosifying or thickening) to gelling a continuous phase (creating a three dimensional structure at the molecular level which 'traps' the continuous phase) and includes the possibility of generating liquid crystal like phases in the continuous phase, all of which can enhance the stability of dispersed phases in the continuous phase. The structurant provides structure in the oil based formulations of the invention which improves the stability of the dispersion of the agrochemical active. Correspondingly in describing oil phases as 'structured' it will be understood to mean that solids dispersed in a structured oil phase show a much lower tendency to settle or segregate from the oil continuous phase than in the absence of the structurant.

Generally the structure is provided by gelling the oil phase and it is usually possible to measure the yield stress of the gelled oils. The yield stress enables the gelled oil to provide support for dispersed agrochemical active thus stabilising the dispersions, with the suspended solids showing a reduced tendency to settle out of suspension or separate from the oil phase. It is possible for the gel to be 'amorphous' in which case it will not generally show a well-defined yield stress, but it rheological properties provide support for the dispersed agrochemical. The structured oil based formulations of the present invention show desired shear thinning properties, even at relatively low shear rates, and this aids pouring or pumping of the structured oil based concentrate and its dilution in water.

The structurant of the present invention is a polyamide formed from dicarboxylic acid comprised from a dimer acid compound, and one or more diamine compounds.

The structurant may optionally be formed with polyol to form polyesteramide. The structurant may also be optionally terminated by amide or by ester groups, in particular where monoalcohols may be used for ester termination and monoamines for amide termination. It is envisaged that the structurant may both be formed with diol and terminated by ester or amide groups to form ester terminated polyesteramide, or amine terminated polyesteramide. The polyamide may therefore be non-end group terminated polyamide, an ester terminated polyamide, an amide terminated amide, a non-end group terminated polyesteramide, an ester terminated polyamide, or an amide terminated polyamide.

In one embodiment the polyamide may be a polyamide formed from and/or comprises the reaction products of a dicarboxylic acid comprised from a dimer acid compound, one or more diamine compounds, optionally diol, optionally monoamine, and optionally monoalcohol. The polyamide may be a polyamide obtainable by reacting a dicarboxylic acid comprised from a dimer acid compound, one or more diamine compounds, optionally diol, optionally monoamine, and optionally monoalcohol.

The polyamide may be formed from the reaction products consisting essentially of a dicarboxylic acid comprised from a dimer acid compound, one or more diamine compounds. The polyamide may be formed from the reaction products consisting of a dicarboxylic acid comprised from a dimer acid compound, one or more diamine compounds. For both such alternatives, the reaction products may optionally include monoamine where amide terminated polyamide is desired, monoalcohol where ester terminated polyamide is desired, and/or diol where polyesteramide is desired.

The dicarboxylic acid is comprised from a dimer acid compound. The term dimer acid (also sometimes referred to as dimer fatty acid or dimer fatty diacid) is well known in the art, and refers to the dimerisation products of mono- or polyunsaturated fatty acids and/or esters thereof. The dimer acid is a difunctional residue (dicarboxylic) which is or includes residues based on fatty acid dimer residues. Dimer acids are the well known mainly dimeric oligomerisation products derived from unsaturated fatty acids (industrially principally oleic, linoleic and/or linolenic acids), typically thermally oligomerised using clay catalysts. Generally the dimer acids have average molecular weights corresponding to approximately two molecules of the starting fatty acid, so dimerised oleic acid has an average molecular weight corresponding to a nominally $C_{36}$ diacid. As manufactured, dimer acids have unsaturation, typically corresponding to 1 or 2 ethylenic double bonds per molecule, but this may be reduced (hydrogenated) in making starting materials for the oligomers used in this invention.

Dimer acids are described T. E. Breuer, 'Dimer Acids', in J. I. Kroschwitz (ed.), Kirk-Othmer Encyclopedia of Chemical Technology, 4th Ed., Wily, New York, 1993, Vol. 8, pp. 223-237. They are prepared by polymerising fatty acids under pressure, and then removing most of the unreacted fatty acid starting materials by distillation. The final product usually contains some small amounts of mono fatty acid, trimer fatty acids, and possibly higher oligomers, but is mostly made up of dimer acids. Hence it is generally referred to as dimer acid. The resultant product can be prepared with various proportions of the different fatty acids as desired.

The dimer acids used in the present invention are preferably derived from the dimerisation products of $C_{10}$ to $C_{30}$ fatty acids, more preferably $C_{12}$ to $C_{24}$ fatty acids, particularly $C_{14}$ to $C_{22}$ fatty acids, further preferably $C_{16}$ to $C_{20}$ fatty acids, and especially $C_{18}$ fatty acids. Thus, the resulting dimer acids preferably comprise in the range from 20 to 60, more preferably 24 to 48, particularly 28 to 44, further preferably 32 to 40, and especially 36 carbon atoms.

The fatty acids, from which the dimer acids are derived, may be selected from linear or branched unsaturated fatty acids. The unsaturated fatty acids may be selected from fatty acids having either a cis/trans configuration, and may have one or more than one unsaturated double bonds. Preferably, the fatty acids used are linear monounsaturated fatty acids.

Suitable dimer acids are preferably derived from (i.e. are the dimer equivalents of) the dimerisation products of oleic acid, linoleic acid, linolenic acid, palmitoleic acid, or elaidic acid. In particular, suitable dimer acids are derived from oleic acid.

The dimer acids may be dimerisation products of unsaturated fatty acid mixtures obtained from the hydrolysis of natural fats and oils, e.g. sunflower oil, soybean oil, olive oil, rapeseed oil, cottonseed oil, or tall oil.

The molecular weight (weight average) of the dimer acid is preferably in the range from 450 to 690, more preferably 500 to 640, particularly 530 to 610, and especially 550 to 590.

The ratio of dimer acids to trimer acids can be varied, by modifying the processing conditions and/or the unsaturated fatty acid feedstock. The dimer acid may be isolated in substantially pure form from the product mixture, using purification techniques known in the art, or alternatively a mixture of dimer acid and trimer acid may be employed.

The dimer acid used in the present invention preferably may have a dimer acid (or dimer) content of greater than 70 wt. %, more preferably greater than 80 wt. %, particularly greater than 85 wt. %, and especially greater than 90 wt. %. Most preferably, the dimer content of the dimer acid is in the range from 90 wt. % to 99 wt. %.

In addition, particularly preferred dimer acids may have a trimer acid (or trimer) content of less than 30 wt. %, more preferably less than 20 wt. %, particularly less than 15 wt. %, and especially less than 10 wt. %.

Furthermore, the dimer acid preferably comprises less than 10 wt. %, more preferably less than 6 wt. %, particularly less than 4 wt. %, and especially less than 3.5 wt. % of monoacid (monomer) or other oligomers of the fatty acid.

All of the above weight percentage values are based on the total weight of polymerised fatty acids and mono fatty acids present.

In another embodiment of the invention, the dicarboxylic acid used to prepare the polyamide is a mixture of the dimer acid and 'co-dicarboxylic acid', where the term co-dicarboxylic acid simply refers to any dicarboxylic acid excluding dimer acid, and the co-dicarboxylic is therefore not formed from fatty acids as described above.

A preferred co-dicarboxylic acid is a linear dicarboxylic of the formula HOOC—$R^1$—COOH wherein $R^1$ is a linear $C_{4-12}$ hydrocarbon, and more preferably a linear $C_6$-$C_8$ hydrocarbon group. Linear di-acids suitable for the present invention include 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedioic acid, 1,12-dodecanedioic acid (1,10-decanedicarboxylic acid), 1,13-tridecanedioic acid (brassylic acid), and 1,14-tetradecanedioic acid (1,12-dodecanedicarboxylic acid).

Another suitable co-dicarboxylic acid for use in the present invention is the reaction product of acrylic or methacrylic acid (or the ester thereof, with a subsequent hydrolysis step to form an acid) and an unsaturated fatty acid. For example, a $C_{21}$ co-dicarboxylic acid of this type may be formed by reacting acrylic acid with a $C_{18}$ unsaturated fatty acid (e.g. oleic acid), where an ene-reaction occurs between the reactants. A specific suitable example of a $C_{21}$ co-dicarboxylic acid is commercially available from Westvaco Corporation, under product number 1550.

Aromatic diacids may be used as the co-dicarboxylic acid. An 'aromatic diacid' as used herein is a molecule having two carboxylic acid groups (—COOH) or reactive equivalents thereof (e.g. acid chloride (—COCl) or ester (—COOR)) and at least one aromatic ring (Ar). Phthalic acids, e.g. isophthalic acid and terephthalic acid, are exemplary aromatic diacids. The aromatic diacid may contain aliphatic carbons bonded to the aromatic ring(s), as in HOOC—CH2-Ar—CH2-COOH and the like. The aromatic diacid may contain two aromatic rings, which may be joined together through one or more carbon bonds, (e.g. biphenyl with carboxylic acid substitution) or which may be fused (e.g. naphthalene with carboxylic acid substitution).

The diamine reactant has two amine groups, both of which are preferably primary amines, and is represented by the formula H($R^3$)N—$R^2$—N($R^4$)H.

$R^2$ may be a hydrocarbon group having at least two carbon atoms, where the carbon atoms may be arranged in a linear, branched, or cyclic fashion, and the group may be saturated or unsaturated. Thus, $R^2$ may be aliphatic or aromatic. $R^2$ may have 2 to 36 carbon atoms, more preferably 2 to 12 carbon atoms, and most preferably hydrocarbon groups having 2 to 6 carbon atoms. $R^3$ and $R^4$ may each represent hydrogen.

Suitable diamines having hydrocarbon $R^2$ groups may be selected from ethylenediamine (EDA), 1,2-diaminopropane, 1,3-diaminopropane, 1,4-diaminobutane, 1,2-diamino-2-methylpropane, 1,3-diaminopentane, 1,5-diaminopentane, 2,2-dimethyl-1,3propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,2, 1,3, and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminonaphthalene (all isomers, including 1,5, 1,8, and 2,3), and 4-amino-2,2,6,6-tetramethylpiperidine.

Suitable aromatic diamines (by which is meant molecules having two reactive, preferably primary amine groups and at least one aromatic ring may be selected from xylene diamine and naphthalene diamine (all isomers).

The $R^2$ group of the diamine may contain oxygen atoms in the form of a polyalkylene oxide group, in which case the diamine may be referred to as a co-diamine. Exemplary polyalkylene oxide-based co-diamines include, without limitation, the JEFFAMINE diamines, i.e. poly(alkyleneoxy)diamines from Texaco, Inc. (Houston, Tex.), also known as polyether diamines. Preferred polyalkylene oxide containing co-diamines are the JEFFAMINE ED and D series diamines. In particular, small amounts of a polyalkylene oxide-based diamine with a major amount of hydrocarbon-based diamine may be preferred. In general, the diamine reactant may be a pure diamine as described above, or a mixture of such diamines.

The $R^2$ group of the diamine may contain nitrogen atoms, where these nitrogen atoms are preferably secondary or tertiary nitrogen atoms. A typical nitrogen atom-containing $R^2$ group having secondary nitrogen atoms may be a polyalkylene amine, i.e. a group containing alternating alkylene groups and amine groups (i.e. —NH— groups). The alkylene group is preferably ethylene, and the polyalkylene amine may be represented by the formula $NH_2$—$(CH_2CH_2NH)_mCH_2CH_2$—$NH_2$ wherein m is an integer from 1 to about 5.

Preferred examples of such diamines may be selected from diethylenetriamine (DETA) and triethylenetetraamine (TETA). When the diamine contains two primary amines in addition to secondary amines, the sturcturant forming reaction is preferably conducted at relatively low temperature, so that the primary amines (in preference to the secondary amines) react with the dimer acid component.

The nitrogen atoms in the nitrogen-containing $R^2$ group may also be present as tertiary nitrogen atoms, e.g. they may be present in a heterocycle of the formula:

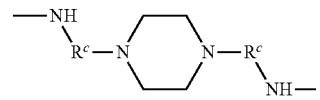

wherein $R^c$ is a $C_{13}$ alkyl group. Bis(aminoethyl)-N,N'-piperazine and bis(aminopropyl)-N,N'-piperazine may be used to introduce these $R^2$ groups into the structurant molecule, and these are such co-diamines according to the invention. In addition, the co-diamine may have one primary amine group and one secondary amine group (e.g. N-ethylethylenediamine or 1-(2aminoethyl)piperazine). Generally, it is preferred that amine compounds having secondary amines not be present in the reaction mixture to any great extent, because their incorporation into an ester terminated polyamide tends to provide for poorer gelling ability for ester-terminated polyamides.

Particularly preferred diamines may be selected from ethylenediamine (EDA), 1,2-diaminopropane, 1,3-diaminopropane, 1,4-diaminobutane, 1,2-diamino-2-methylpropane, 1,3-diaminopentane, 1,5-diaminopentane, and 1,6-hexanediamine. More preferably, ethylenediamine, 1,2-diaminopropane, 1,3-diaminopropane, and 1,4-diaminobutane. Most preferably, ethylenediamine.

Diamines wherein $R^3$ and $R^4$ are not hydrogen, and/or wherein $R^2$ is not a hydrocarbon, may be referred to herein as co-diamines. When present, co-diamines are preferably used in a minor amount compared to the diamines.

The groups $R^3$ and $R^4$ preferably represent hydrogen, but may also independently represent an alkyl group. Preferably, the alkyl group is a $C_{1-10}$ alkyl, more preferably a $C_{1-5}$ alkyl, most preferably a $C_{1-3}$ alkyl.

The groups $R^3$ and $R^4$ may alternatively join together, or join together with $R^2$ to form a heterocyclic structure. For example, when piperazine is used as a co-diamine, the $R^3$ and $R^4$ groups will have joined together to form an ethylene bridge.

Where polyesteramide is used as the structurant, polyol is also included in the reaction component mixture.

The term polyol is well known in the art, and refers to an alcohol comprising more than one hydroxyl group. Preferably the polyol is a $C_2$ to $C_{20}$ polyol. More preferably, a $C_2$ to $C_8$ polyol, further preferably $C_3$ to $C_7$ polyol residue. Especially preferred are $C_5$ to $C_6$ polyol residues. The polyol may be linear, branched, partially cyclic, or cyclic.

The polyol may have in the range from 2 to 9 hydroxyl groups. Preferably, in the range from 2 to 8. More preferably, in the range from 2 to 7. Most preferably, in the range from 2 to 6.

The polyol may be selected from diols, triols, tetrols, pentols, hexols, heptols, octols, or nonols. Preferably, the polyol may be selected from diols, triols, tetrols, pentols, hexols, or heptols. More preferably, the polyol is a diol or a triol. Most preferably, a diol.

Suitable polyols for use in preparing the polyesteramide may be selected from ethylene glycol, propylene glycol, butylene glycol, glycerol, trimethylolpropane, pentaerythritol, neopentyl glycol, tris (hydroxylmethyl) methanol, dipentaerythritol, and tripentaerythritol.

In particular, diols represented by the formula HO—$R^5$—OH may be preferred. $R^5$ may be a hydrocarbon group having at least two carbon atoms, where the carbon atoms may be arranged in a linear, branched, or cyclic fashion, and the group may be saturated or unsaturated. Thus, $R^5$ may be aliphatic or aromatic. $R^5$ may have 2 to 16 carbon atoms, more preferably 2 to 10 carbon atoms, and most preferably hydrocarbon groups having 3 to 6 carbon atoms.

Suitable diols for use in preparing the polyesteramide may be selected from ethylene glycol, propylene glycol, butylene glycol, or neopentyl glycol. A preferred diol is neopentyl glycol.

Where the polyamide is ester terminated, monoalcohols may be used to effect said termination.

The monoalcohol may be represented by the formula $R^6$—OH, wherein $R^6$ is a hydrocarbon group having at least four carbon atoms. Thus, the monoalcohol can also be described as a monohydric alcohol.

$R^6$ is preferably a $C_{10-36}$ hydrocarbon, more preferably a $C_{12-24}$ hydrocarbon, further preferably a $C_{16-22}$ hydrocarbon, and most preferably is a $C_{18}$ hydrocarbon. As used herein, the term $C_{10-36}$ refers to a hydrocarbon group having at least 10, but not more than 36 carbon atoms, and similar terms have an analogous meaning.

The carbon atoms of the $R^6$ group may be arranged in a linear, branched or cyclic fashion, and the group may be saturated or unsaturated. Preferably, $R^6$ is linear, with the hydroxyl group located on a terminal carbon atom, i.e. the monoalcohol is a primary saturated monoalcohol. Suitable primary saturated monoalcohols may be selected from 1-dodecanol, 1-tetradecanol, 1-hexadecanol (cetyl alcohol), 1-octadecanol (stearyl alcohol), 1-eicosanol (arachidyl alcohol), and 1-docosanol (behenyl alcohol).

The $R^6$ monoalcohol may alternatively contain an alkenyl group, i.e. an alkyl group having unsaturation between at least any two adjacent carbon atoms. One or a mixture of these alcohols may be used to prepare the ester terminated polyamide.

Another monoalcohol reactant suitable for forming ester terminated polyamides for the invention is a Guerbet alcohol. Guerbet alcohols have the general formula H—C($R^7$)($R^8$)—$CH_2$—OH wherein $R^7$ and $R^8$ may be the same or different, and preferably each independently represent a $C_{6-12}$ hydrocarbon group. Further discussion of Guerbet alcohols may be found in, e.g., "Dictionary For Auxiliaries For Pharmacy, Cosmetics And Related Fields," H. P. Fiedler, 3rd Ed., 1989, Editio Cantor Aulendorf. A preferred Guerbet alcohol for use in the present invention is 2-hexadecyloctadecanol which has 24 carbon atoms.

As $R^6$ is a hydrocarbon, the monoalcohol is a monofunctional reactant under the reaction conditions employed to prepare the resin of the invention (as discussed later). Furthermore, under preferred reaction conditions, $R^6$—OH is the only monofunctional reactant used to form the polyamide. Thus, a reactant mixture useful in preparing ester terminated polyamide preferably does not contain monocarboxylic acid (i.e. an organic molecule containing a single carboxylic acid group) and/or monoamine (i.e. an organic molecule containing a single amine group).

Particularly preferred monoalcohols may be selected from 1-hexadecanol (cetyl alcohol), 1-octadecanol (stearyl alcohol), 1-eicosanol (arachidyl alcohol), and 1-docosanol (behenyl alcohol). Preferably, 1-octadecanol (stearyl alcohol) or 1-docosanol (behenyl alcohol).

Where the polyamide is amide terminated, monoamines may be used to effect said termination. By monoamines it will be understood that this refers to molecules having one —NH functionality per molecule. The terminal groups of the polyamide are secondary or tertiary amide groups, and these will be understood to be formed from primary or secondary monoamines respectively, i.e. having formula HN—$R^9R^{10}$, where at least one of the groups $R^9$ and $R^{10}$ groups is not hydrogen for a primary monoamine, and where both of the groups $R^9$ and $R^{10}$ groups are not hydrogen for a secondary monoamine. Secondary monoamines, and therefore tertiary amide terminal groups, are preferred.

Groups $R^9$ and $R^{10}$ may each independently be selected from a hydrocarbon group, and preferably represent an alkyl or alkenyl group which contain at least 1 carbon atom, and preferably, more than 4 carbon atoms. The upper range for the number of carbon atoms in each $R^9$ and $R^{10}$ group is preferably less than or equal to about 28 carbon atoms. The groups $R^9$ and $R^{10}$ may each independently have 1-28 carbon atoms. Preferably, 4-26 carbon atoms, more preferably 10-24 carbon atoms, further preferably 14-22 carbon atoms. Most preferably, from 14-18 carbon atoms.

Preferred monoamines are those which provide for di-$C_{14-18}$ alkyl amide terminating groups. Particularly preferred monoamines may be selected from ditetradecyl amine, dipentadecyl amine, dicetyl amine, diheptadecyl amine, and distearyl amine.

Alkyl groups are preferred, however alkenyl groups having 1-3, and preferably 1 site of unsaturation, are also suitable.

The amide terminating groups may be formed by adding secondary monoamine as a co-reactant in preparing the polyamide. Suitable secondary monoamines are commercially available from a variety of sources, including Witco Corporation (USA); Akzo Nobel Chemicals, Surface Chemistry (USA); and Aldrich (USA). Ditallow amine is a particularly preferred secondary monoamine.

Particularly preferred structurants are those selected from ester terminated polyamide, amide terminated polyamides, and ester terminated polyesteramides.

Suitable specific structurants may be selected from:
ester terminated polyamide formed from $C_{36}$ dimer acid, ethylenediamine, and behenyl alcohol or stearyl alcohol;
amide terminated polyamides formed from $C_{36}$ dimer acid, ethylenediamine, and ditetradecyl amine or dipentadecyl amine or dicetyl amine or diheptadecyl amine or distearyl amine; and
ester terminated polyesteramides formed from $C_{36}$ dimer acid, ethylenediamine, neopentyl glycol, and behenyl alcohol or stearyl alcohol.

Reactive equivalents of dimer acids and/or diamines may be used to form the polyamide. For example, diesters may be substituted for some or all of the diacid, where 'diesters' refer to the esterification product of diacid with hydroxyl-containing molecules. However, such diesters are preferably prepared from relatively volatile hydroxyl-containing molecules, in order that the hydroxyl-containing molecule may be easily removed from the reaction vessel subsequent to monoalcohol and/or diamine (both as defined herein) reacting with the diester. A lower alkyl diester, e.g. the esterification or diesterification product of diacid as defined herein and a $C_{1-4}$ monohydric alcohol (e.g. methanol, ethanol, propanol and butanol), may be used in place of some or all of the dimer acid in the structurant forming reaction.

An acid halide of the dimer acid may likewise be employed in place of some or all of the dimer acid. However such a material is typically much more expensive and difficult to handle compared to the dimer acid, and thus the dimer acid itself is preferred. Likewise, the monoalcohol may be esterified with a volatile acid, e.g. acetic acid, prior to being employed in the structurant forming reaction of the invention. While such reactive equivalents may be employed in the reaction, their presence may not preferred as such equivalents may introduce undesired reactive groups into the reaction vessel.

In preparing a structurant of the present invention, the above-described reactants may be combined in any order. Preferably, the reactants are simply mixed together and heated for a time and at a temperature sufficient to achieve essentially complete reaction, to thereby form the structurant. The terms 'complete reaction' and 'reaction equilibrium' as used herein have essentially the same meaning, namely that further heating of the product resin does not result in any appreciable change in the performance characteristics of the product resin, where the most relevant performance characteristic is the ability of the structurant to form a clear, firm gel upon being combined with the oil system.

The structurant may be formed in a one-step procedure, wherein all of the dimer acid (including optionally co-dicarboxylic acid), diamine (including optionally co-diamine), and optionally monoalcohol, monoamine, and polyol are combined and then heated to about 200-250° C. for a few hours, typically 2-8 hours. As one or more of the reactants may be a solid at room temperature, it may be convenient to combine each of the ingredients at a slightly elevated temperature, and then form a homogeneous mixture prior to heating the reaction mixture to a temperature sufficient to cause reaction between the components.

Alternatively, although less preferably, two of the reactants may be combined and reacted together, and then further reactants are added followed by further heating to obtain the structurant. Reaction progress may be conveniently monitored by periodically measuring the acid and/or amine number of the product mixture. As one example, the dimer acid may be reacted with the diamine so as to form polyamide, and then this intermediate polyamide may be reacted with monoalcohol to form ester-terminated polyamide. Alternatively, the dimer acid may be reacted with the monoalcohol to form diester, and this diester may be reacted with diamine to form an ester-terminated polyamide.

Any catalyst that may accelerate amide formation between carboxylic acid and amine groups, may be present in the reaction mixture described above. Thus, mineral acid such as phosphoric acid, or tin salts such as dibutyltin oxide, may be present during the reaction. In addition, it is preferred to remove water from the reaction mixture as it is formed upon amide and ester formation. This is preferably accomplished by maintaining a vacuum on the reacting mixture.

It is important to control the stoichiometry of the reactants in order to prepare polyamide according to the invention. In the following discussion, the terms 'equivalent(s)' and 'equivalent percent' will be used. The term equivalents refers to the number of reactive groups present in a molar quantity of a molecule, such that a mole of a dicarboxylic acid (e.g., sebacic acid) has two equivalents of carboxylic acid, while a mole of monoalcohol and monoamine have one equivalent of hydroxyl and amine respectively. Furthermore, it is emphasised that the dimer acid has only two reactive groups (both carboxylic acids), the monoalcohol and monoamine have only one reactive group each, and the diamine has only two reactive groups (preferably both primary amines), and these are preferably, although not necessarily, the only reactive materials present in the reaction mixture.

According to the invention, is it preferred that the equivalents of carboxylic acid are substantially equal to the combined equivalents of hydroxyl contributed by monoalcohol or monoamine, and amine contributed by diamine. In other words, if the reaction mixture used to form the structurant has "x" equivalents of carboxylic acid, "y" equivalents of amine and "z" equivalents of monoalcohol or monoamine, then $0.9<\{x/(y+z)\}<1.1$ and preferably $\{x/(y+z)\}$ is substantially 1.0. Under these conditions, substantially all of the carboxylic acid groups will react with substantially all of the hydroxyl and amine groups, so that the final product contains very little unreacted carboxylic acid, hydroxyl, or amine groups. In other words, each of the acid and amine numbers of a resin of the invention is preferably less than about 25, is more preferably less than about 15, and is more preferably less than about 10, and is still more preferably less than about 5.

When co-dicarboxylic acid is employed to prepare the structurant, the co-dicarboxylic acid preferably contributes no more than about 50% of the equivalents of carboxylic acid present in the reaction mixture. Stated another way, the co-dicarboxylic acid contributes from 0-50 equivalent percent of the acid equivalents in the reaction mixture. Preferably, the co-dicarboxylic acid contributes 0-30 equivalent percent, and more preferably contributes 0-10 equivalent percent of the acid equivalents in the reaction mixture.

When co-diamine is employed to prepare the structurant, the co-diamine present in the reaction mixture. Stated another way, the co-diamine contributes from 0-50 equivalent percent of the amine equivalents in the reaction mixture. Preferably, the co-diamine contributes 0-30 equivalent percent, and more preferably contributes 0-10 equivalent percent of the amine equivalents in the reaction mixture.

The amount of structurant present in the concentrate may preferably be at least 0.5 wt. %. More preferably, 1.0 wt. %. Further preferably, 2.0 wt. %. More further preferably, 2.5 wt. %. Most preferably, 3.0 wt. %. The amount of structurant present in the concentrate may preferably be less than 10.0 wt. %. More preferably, 8.0 wt. %. Further preferably, 6.0 wt. %. Most preferably, 4.0 wt. %.

It will be understood that the preferred lower and higher amounts of the structurant present in the concentrate may be considered separately, or may be in any combination.

Structurants of the invention may be solids with melting points in the range from 60° C. to 110° C. Preferably, in the range from 70° C. to 100° C. More preferably, in the range from 75° C. to 95° C. Most preferably, in the range from 80° C. to 85° C.

The structurant is preferably derived from renewable and/or bio-based sources. The level of this may be determinable by ASTM D6866 as a standardised analytical method for determining the bio-based content of samples using $^{14}C$ radiocarbon dating. ASTM D6866 distinguishes carbon resulting from bio-based inputs from those derived from fossil-based inputs. Using this standard, a percentage of carbon from renewable sources can be calculated from the total carbon in the sample.

Preferably, the structurant has a renewable carbon content of at least 60 wt. % when determined using ASTM D6866 and as a percentage of the total organic carbon present in the structurant. More preferably, at least 75 wt. %. Further preferably, at least 85%. Most preferably, at least 90 wt. %.

The acid value of the structurants of the present invention may be in the range from 0 $mg(KOH) \cdot g^{-1}$ to 26 $mg(KOH) \cdot g^{-1}$. Preferably, in the range from 2 $mg(KOH) \cdot g^{-1}$ to 20 $mg(KOH) \cdot g^{-1}$. More preferably, in the range from 4 $mg(KOH) \cdot g^{-1}$ to 16 $mg(KOH) \cdot g^{-1}$.

To determine acid values, a test sample dissolved in a suitable solvent (usually ethanol) is titrated against standard (usually ethanolic) KOH solution with phenophthalein indicator. The acid value was measured using the A.O.C.S. Official method Te 1a-64 (Reapproved 1997), and expressed as the number of milligrams of potassium hydroxide required to neutralise the free fatty acids in 1 g of sample. The results are quoted as "Acid Value" in $mg(KOH) \cdot g^{-1}$.

The structurant has an amine value in the range from 0 $mg(KOH) \cdot g^{-1}$ to 2 $mg(KOH) \cdot g^{-1}$, more preferably from 0.2 $mg(KOH) \cdot g^{-1}$ to 1 $mg(KOH) \cdot g^{-1}$.

Oil dispersions will be understood to refer concentrates where the agrochemical active is dispersed as solid particles in an oil phase. In this context the term oil is used to cover agrochemically acceptable non-aqueous organic liquids used as dispersion carrier fluids in such formulations. Many of these will be immiscible with water and conventionally regarded as 'oils' e.g. mineral and other hydrocarbon oils and ester oils, some may be water miscible e.g. lower alkanols, or hydroxylic e.g. fatty alcohols, glycols or liquid polyols, or otherwise may not usually be thought of as oils.

The term 'oil' is used for such carrier fluids as a convenient term. Generally oil dispersion formulations are made so that they emulsify readily on dilution with water, desirably with just the agitation required to dilute the formulation.

The oil of the concentrate will be understood to preferably form the continuous phase of the concentrate. The oil is preferably a liquid at room temperature and pressure.

A wide range of oils (carrier fluids) can be structured using the compounds of the invention and the best such compounds will provide structuring in a wide range of oils (rather than a relatively narrow range for each structuring compound). The range of oil polarity for which structuring can be provided is wide ranging from non-polar oils such as paraffinic oils to alkoxylate oils. One way of expressing this range of polarity is to use a numeric solubility parameter. It has been found that Hansen and Beerbower solubility $\delta^t$ parameter combining dispersive (van der Waals), polar (Coulombic) and hydrogen bonding component (see the CRC Handbook of Solubility Parameters and Other Cohesion Parameters p85 to 87) provide good correspondence with the polarity as reflected in the performance of the oils that we have investigated.

The numerical values of solubility parameter given below are Hansen and Beerbower $\delta^t$ values abbreviated as "HBSP" values. Generally structurants of and used in this invention can provide structure in oils with HBSP values ranging from 12 (very non-polar) to 22 (highly polar), particularly from 14 to 20.

Typical oils that can be structured using compounds of the invention include:

liquid and low-melting temperature alcohols including relatively short chain alkanols such as t-butanol and pentanol, medium chain alcohols such as 2-ethylhexanol and 2-ethyl-1,3 hexanediol, long chain alcohols such as isodecanol, isotridecanol, cetyl alcohol, oleyl alcohol, octyldodecanol, liquid $C_8$ to $C_{32}$ alcohols e.g. Guerbet alcohols such as Isofol 24; liquid polyols such as glycols and (poly)glycerol; aromatic alcohols such as benzyl alcohol; polycyclic alcohols such as abietyl alcohol;

branched liquid fatty alcohols, particularly Guerbet alcohols e.g. octyldodecanol or isostearyl alcohol (see above) e.g. the isostearyl alcohol available from Croda under the trade mark Prisorine 3515 (HBSP 17.9);

fatty alcohol polyalkoxylates, particularly propoxylates such as the alkoxylates of $C_{12}$ to $C_{20}$ fatty, particularly $C_{14}$, $C_{16}$ and $C_{18}$ fatty alcohols which can be linear e.g. as in palmitic and stearic acids, or branched e.g. as in isostearyl alcohol (in practice a product typically derived from dimer acid manufacture which contains a mixture of mainly branched $C_{14}$ to $C_{22}$ alcohols averaging about $C_{18}$), with from 3 to 25 particularly from 7 to 20 alkoxylate alkoxylate, especially ethoxylate, propoxylate or mixtures of ethoxylate and propoxylate, units e.g. the stearyl alcohol 15-polypropoxylate available from Croda under the trade mark Arlamol E (HBSP 20.8);

ester oils particularly those based on $C_2$ to $C_{30}$ linear, branched or unsaturated fatty acids and linear, branched or unsaturated fatty alcohols, and typically esters derived from monocarboxylic acid(s) with monohydric alcohol(s); di- or tri-carboxylic acid(s) with monohydric alcohol(s); or di- or poly-hydric alcohol(s) with mono-carboxylic acid(s), e.g. the glycerol tris-2-ethylhexanoate ester oil available from Croda under the trade mark Estol 3609 (HBSP 20.4), the isopropyl isostearate oil available from Croda under the trade mark Prisorine 2021 (HBSP 17.7) the methyl oleate oil available from Croda under the trade mark Priolube 1400 (HBSP 17.9), methyl caprylate, alkyl acetate esters, particularly $C_6$ to $C_{13}$ alkyl acetates, and especially where the alkyl groups are oxo-alcohol residues, e.g. the ester oils available under the trade mark Exxate from Exxon, synthetic triglyceride esters such as glycerol tri-($C_8$ to $C_{24}$)ates e.g. glycerol tricaprylate such as Estasan 3596, glyceryl trioleate such as Priolube 1435, both available from Croda, and glycerol tri ricinoleate, PEG oleate and isostearate, isopropyl laurate or isostearate, trimethylpropane triesters e.g. with mixed $C_8/C_{10}$, stearic or oleic acids; natural triglycerides such as rape seed (canola) oil, soya oil, sunflower oil, and fish oil;

methylated natural triglycerides such as methylated rape seed, soya and/or sunflower oils;

aromatic ester oils, particularly esters if benzoic acid and $C_8$ to $C_{18}$ monohydric alcohol(s) e.g. the $C_{12}$ to $C_{15}$ benzoate oil from Finetex under the trade mark Finsolve TN (HBSP 19.1);

branched liquid fatty alcohols, particularly Guerbet alcohols e.g. octyldodecanol or isostearyl alcohol (see above) e.g. the isostearyl alcohol available from Croda under the trade mark Prisorine 3515 (HBSP 17.9);

branched liquid fatty acids, particularly isostearic acid and dimer acid (dimerised fatty acids, particularly oleic and/or linoleic acids), such as dilinoleic acid (HBSP 17.8); and hydrocarbons including toluene, xylene, and liquid paraffinic materials such as hexane, octane, gasoline, diesel, liquid hydrocarbon waxes, lamp oil, paraffinic oils such as Sunspray 6N, 8N and 11N from Sunoco and Puccini 19P from Q8, (iso)-paraffinic oils such as Isopar V and Exxol D140 from ExxonMobil, and aromatic mineral oils such as the alkyl benzenes available from ExxonMobil under the Solvesso brand;

miscellaneous liquids such as isophorone (3,3,5-trimethyl-2-cyclohexene-1-one), liquid (at 25° C.) fatty acids such as caprylic, isostearic, oleic, and vegetable oil fatty acids, ketones such as methyl ethyl ketone (MEK), aldehydes such as butanal.

The liquids (for convenience referred to generically as 'oils'), particularly as set out above can be used as mixtures of two or more different types of oils.

Of course, as the formulation type is oil based suspensions of active ingredients, it follows that the oil may not be a solvent for the dispersed active, so the choice of oil will complement the desired active(s) in any particular formulation.

It is envisaged that the amount of oil in the concentrate may be determined by the user and set according to the needs of the formulation. A feature of the present invention is the wide range of amounts of oil that can be present in a concentrate and structured. Therefore, the concentrate may comprise oil in the amount in the range from 10 wt. % to 98 wt. %.

In particular, concentrates which include micronutrients typically have high loadings of micronutrients and therefore lower amounts of oil. In micronutrient concentrates the amount of oil in the concentrate may be in the range from 20 wt. % to 60 wt. %, more preferably in the range from 30 wt. % to 50 wt. %. In an alternative embodiment where the concentrate comprises agrochemical actives, the amount of active may be typically of the order of a few percent, and therefore the amount of oil in the concentrate may be at least 50 wt. %, more preferably in the range from 60 wt. % to 98 wt. %, further preferably in the range from 70 wt. % to 85 wt. %.

The agrochemical active may preferably be a solid phase agrochemical active. Solid agrochemical active compounds are to be understood in the present invention as meaning all substances customary for plant treatment, whose melting point is above 20° C. (at standard pressure). Solid agrochemical actives will also include insoluble active ingredients, i.e. active ingredients whose solubility in water is such that a significant solid content exists in the concentrate after addition.

Agrochemical actives refer to biocides which, in the context of the present invention, are plant protection agents, more particular chemical substances capable of killing different forms of living organisms used in fields such as medicine, agriculture, forestry, and mosquito control. Also counted under the group of biocides are so-called plant growth regulators.

Biocides for use in agrochemical formulations of the present invention are typically divided into two sub-groups:
pesticides, including fungicides, herbicides, insecticides, algicides, moluscicides, miticides, and rodenticides; and
antimicrobials, including germicides, antibiotics, antibacterials, antivirals, antifungals, antiprotozoals, and antiparasites.

In particular, biocides selected from insecticides, fungicides, or herbicides may be particularly preferred.

The term 'pesticide' will be understood to refer to any substance or mixture of substances intended for preventing, destroying, repelling, or mitigating any pest. A pesticide may be a chemical substance or biological agent (such as a virus or bacteria) used against pests including insects, plant pathogens, weeds, mollusks, birds, mammals, fish, nematodes (roundworms), and microbes that compete with humans for food, destroy property, spread disease or are a nuisance. In the following examples, pesticides suitable for the agrochemical compositions according to the present invention are given.

A fungicide is a chemical control of fungi. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies.

Examples for suitable fungicides, according to the present invention, encompass the following species: (3-ethoxypropyl)mercury bromide, 2-methoxyethylmercury chloride, 2-phenylphenol, 8-hydroxyquinoline sulphate, 8-phenylmercuri oxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulphide, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulphide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper (II) carbonate, basic, copper fungicides, copper hydroxide, copper naphthenate, copper oleate, copper oxychloride, copper(II) sulphate, copper sulphate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulphon, dinoterbon, diphenylamine, dipyrithione, disulphiram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulph, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, fluopicolide, fluoroimide, fluotrimazole, fluoxastrobin, fluquinconazole, flusilazole, flusulphamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hex achlorobenzene, hex achlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulphocarb, methfuroxam, methyl bromide, methyl isothiocyanate, methylmercury benzoate, methylmercury dicyandiamide, methylmercury pentachlorophenoxide, metiram, metominostrobin, metrafenone, metsulphovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulphamide fungicides, phosdiphen, phthalide, phthalimide fungicides, picoxystrobin, piperalin, polycarbamate, polymeric dithiocarbamate fungicides, polyoxins, polyoxorim, polysulphide fungicides, potassium azide, potassium polysulphide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfiir, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulphide, spiroxamine, streptomycin, strobilurin fungicides, sulphonanilide fungicides, sulphur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide, and mixtures thereof.

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are non-selective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat.

Suitable herbicides may be selected from the group comprising: aryloxycarboxylic acid e.g. MCPA, aryloxyphenoxypropionates e.g. clodinafop, cyclohexanedione oximes e.g. sethoxydim, dinitroanilines e.g. trifluralin, diphenyl ethers e.g. oxyfluorfen, hydroxybenzonitriles e.g. bromoxynil, sulphonylureas e.g. nicosulphuron, triazolopyrimidines e.g. penoxsulam, triketiones e.g. mesotriones, or ureas e.g. diuron.

Particularly preferred herbicides may be selected from 2,4-dichlorophenoxyacetic acid (2,4-D), atrazine, dicamba as benzoic acid, glyphosate, imazapic as imidazolinone, metolachlor as chloroacetamide, picloram, clopyralid, and triclopyr as pyridinecarboxylic acids or synthetic auxins.

An insecticide is a pesticide used against insects in all developmental forms, and includes ovicides and larvicides used against the eggs and larvae of insects. Insecticides are used in agriculture, medicine, industry and the household.

Suitable insecticides may include those selected from:
Chlorinated insecticides such as, for example, Camphechlor, DDT, Hexachloro-cyclohexane, gamma-Hexachlorocyclohexane, Methoxychlor, Pentachlorophenol, TDE, Aldrin, Chlordane, Chlordecone, Dieldrin, Endosulphan, Endrin, Heptachlor, Mirex, and mixtures thereof;

Organophosphorous compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulphoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphosmethyl, Profenofos, Terbufos, Tetrachlorvinphos, Tribufos, Trichlorfon, and mixtures thereof;

Carbamates such as, for example, Aldicarb, Carbofuran, Carbaryl, Methomyl, 2-(1-Methylpropyl)phenyl methylcarbamate, and mixtures thereof;

Pyrethroids such as, for example, Allethrin, Bifenthrin, Deltamethrin, Permethrin, Resmethrin, Sumithrin, Tetramethrin, Tralomethrin, Transfluthrin, and mixtures thereof;

Plant toxin derived compounds such as, for example, Derris (rotenone), Pyrethrum, Neem (Azadirachtin), Nicotine, Caffeine, and mixtures thereof;

Neonicotinoids, such as imidacloprid;

Abamectins, e.g. emamactin;

Oxadiazines, such as indoxacarb;

Anthranilic diamides such as rynaxypyr.

Rodenticides are a category of pest control chemicals intended to kill rodents. Suitable rodenticides may include anticoagulants, metal phosphides, phosphides, and calciferols (vitamins D), and derivatives thereof.

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulphate. A nematicide is a type of chemical pesticide used to kill parasitic nematodes (a phylum of worm).

In the following examples, antimicrobials suitable for agrochemical compositions according to the present invention are given.

Bactericidal disinfectants may include those selected from active chlorines, active oxygen, iodine, concentrated alcohols, phenolic substances, cationic surfactants, strong oxidisers, heavy metals and their salts, and concentrated strong acids and alkalis between pH of from 1 to 13. Suitable antiseptics (i.e., germicide agents that can be used on human or animal body, skin, mucoses, wounds and the like) may include diluted chlorine preparations, iodine preparations, peroxides, alcohols with or without antiseptic additives, weak organic acids, phenolic compounds, and cation-active compounds.

Particular preference is given to active compounds from the classes of the azole fungicides (azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidol, flusilazole, flutriafol, furconazole, furconazole-cis, hexaconazole, imazalil, imazalil sulphate, imibenconazole, ipconazole, metconazole, myclobutanil, nuarimol, oxpoconazole, paclobutrazole, penconazole, pefurazoate, prochloraz, propiconazole, prothioconazole, pyrifenox, simeconazole, tebuconazole, tetraconazole, triadimefon, triadimenol, triflumizole, triforin, triticonazole, uniconazole, voriconazole, viniconazole), strobilurin fungicides (azoxystrobin, dimoxystrobin, fluoxastrobin, kresoxim-methyl, metominostrobin, orysastrobin, picoxystrobin, pyraclostrobin, trifloxystrobin), the SDH fungicides, the chloronicotinyl insecticides (clothianidin, dinotefuran, imidacloprid, thiamethoxam, nitenpyram, nithiazin, acetamiprid, nitenpyram, thiacloprid), the insecticidal ketoenols (spirodiclofen, spiromesifen, spirotetramate), fiproles (fiprole, ethiprole) and butenolides, and also pymetrozine, fluopicolid, N-(3',4'-dichloro-5-fluoro-1,1'-biphenyl-2-yl)-3-(difluoromethyl)-1-methyl-1H-pyrazole-4-carboxamide and N-{2-[3-chloro-5-(trifluoromethyl)-2-pyridinyl]ethyl}-2-(trifluoromethyl)benzamide. Particular preference is also given to herbicides, in particular sulphonylureas, triketones and herbicidal ketoenols, and also safeners.

The structurant of the present invention may be applied to a wide range of insoluble active ingredients (that is to say active ingredients whose solubility in water is such that a significant solid content exists in the concentrate).

Preferred examples of such agrochemical actives may be selected from;

the fungicides tebuconazole, prothioconazole, N-(3',4'-dichloro-5-fluoro-1,1'-biphenyl-2-yl)-3-(difluoromethyl)-1-methyl-1H-pyrazole-4-carboxamide (known from WO 03/070705), N-{2-[3-chloro-5-(trifluoromethyl)-2-pyridinyl]ethyl}-2-(trifluoromethyl)benzamide (known from WO 04/16088), trifloxystrobin, copper oxychloride, fluopicolid, azoxystrobin;

the insecticides thiamethoxam, clothianidin, thiacloprid, spirotetramate, fipronil, ethiprol, carbaryl, cypermethrin;

the herbicides thiencarbazone, sulcotrione, mesotrione, tembotrione, pyrasulphotole, iodosulphuron, mesosulphuron, forarnsulphuron, nicosulphuron, and pyrazosulfuron-ethyl.

Particularly preferred examples of agrochemical actives may be selected from mesotrione, copper oxychloride, or nicosulphuron (sulphonyl urea).

The concentration of the agrochemical active in the concentrate is not critical for the purposes of the present invention, and may be determined by other factors as required. The concentration of the agrochemical active in the is preferably in the range from 0.5 wt. % to 30 wt. %, more usually from 1 wt. % to 20% wt. %, and desirably from 2.5 wt. % to 10% wt. %, by weight of the concentrate. Particular actives may be present in higher amounts. For example, copper oxychloride may typically be present in the concentrate in the amount from 30 wt. % to 60 wt. %.

The concentrate may optionally comprising nutrients in addition to, or as an alternative to, agrochemical actives. In such formulations the nutrient is typically in a dry form.

The nutrients may preferably be a solid phase nutrients. Solid nutrients are to be understood in the present invention as meaning substances whose melting point is above 20° C. (at standard pressure). Solid nutrients will also include insoluble nutrient ingredients, i.e. nutrient ingredients whose solubility in water is such that a significant solid content exists in the concentrate after addition.

Nutrients refer to chemical elements and compounds which are desired or necessary to promote or improve plant growth. Suitable nutrients generally are described as macronutrients or micronutrients. Suitable nutrients for use in the concentrates according to the invention are all nutrient compounds.

Micronutrients typically refer to trace metals or trace elements, and are often applied in lower doses. Suitable micronutrients include trace elements selected from zinc, boron, chlorine, copper, iron, molybdenum, and manganese. The micronutrients may be in a soluble form or included as insoluble solids, and may be salts or chelated.

Macronutrients typically refer to those comprising nitrogen, phosphorus, and potassium, and include fertilisers such as ammonium sulphate, and water conditioning agents. Suitable macro nutrients include fertilisers and other nitrogen, phosphorus, potassium, calcium, magnesium, sulphur containing compounds, and water conditioning agents.

Suitable fertilisers include inorganic fertilisers that provide nutrients such as nitrogen, phosphorus, potassium or sulphur. Fertilisers may be included in diluted formulations at relatively low concentrations or as more concentrated solutions, which at very high levels may include solid fertiliser as well as solution.

It is envisaged that inclusion of the nutrient would be dependent upon the specific nutrient, and that micronutrients would typically be included at lower concentrations whilst macronutrients would typically be included at higher concentrations.

When present, the proportion of nutrient in the total concentrate is typically from 5 wt. % to 60 wt. %, more usually, 10 wt. % to 55 wt. %, particularly 15 wt. % to 50% wt. %.

Agrochemical concentrates are agrochemical compositions, which may be aqueous or non-aqueous, and which are designed to be diluted with water (or a water based liquid) to form the corresponding end-use agrochemical formulations, typically spray formulations. Said concentrates include those in liquid form (such as solutions, emulsions, or dispersions) and in solid form (especially in water dispersible solid form) such as granules or powders.

Accordingly, the concentrate of the present invention may be formulated as an emulsion concentrate (EW), an oil-based suspension concentrate (OD), and/or suspoemulsions (SE). In an OD or SE formulation the active and/or nutrient compound may be present as a solid or emulsified liquid. It is envisaged that the structurant of the present invention will particularly find use in a OD formulation.

The amount of structurant and other components may be present in the concentrate such that the concentrate does not comprise any added water, although some trace amounts of water may be present in any of the components.

The concentrate may be preferably be least 90 wt. % non-aqueous. More preferably, at least 95 wt. %. Further preferably, at least 98 wt. %.

The structurant of the present invention will typically be used in an amount proportional to the amount of the oil in the concentrate. The ratio of structurant to oil in the concentrate is preferably at a weight ratio of from about 1:10 to about 1:100. More preferably, from about 1:20 to about 1:50. This ratio range will generally be maintained for concentrates and in the agrochemical spray formulations.

The structurants of the present invention provide for desired stability of the resulting concentrates. The concentrates do not undergo separation under storage. Additionally, the concentrates return to being homogeneous liquids at room temperature after being frozen.

It has been found that the structuring of the oil based concentrate of the present invention provides excellent stability over time and at various temperatures, and even when the oil based concentrate undergoes shear forces for example on mixing.

The concentrates of the present invention, have a maximum separation of 15% and preferably not more than 10% at an accelerated test over 14 days at 54° C. where the separation is as defined in the Examples. Most preferably, the concentrate has no more than 2% separation of an accelerated test over 14 days at 54° C.

The elastic/storage modulus (denoted as G') is the measure of a sample's elastic behaviour, i.e. a measure of the elastic response of a material and the ability to return to a structured form after being subjected to shear). It will be understood that elastic/storage modulus values described herein are based on rapeseed oil with 3 wt. % structurant, and after a period of 20 minutes once the shear has been reduced to zero.

The elastic/storage modulus value (G') of the concentrate may return to a value after shear less than 20 Pa from the value before shear. Preferably, less than 10 Pa. More preferably less than 5 Pa.

It will be understood that viscosity values defined below are based on rapeseed oil with 3 wt. % structurant. Methods of determining zero-shear viscosity are as described in more detail herein. Zero-shear viscosity will be understood to represent the viscosity at the limit of low shear rate, i.e. the maximum plateau value attained as shear stress or shear rate is reduced, and is effectively the viscosity of the composition whilst at rest.

The zero-shear viscosity of the oxidised cellulose may be in the range from 8,000 to 28,000 Pa·s. Preferably, the zero-shear viscosity is in the range from 10,000 to 25,000 Pa·s. More preferably, the zero-shear viscosity is in the range from 12,000 to 24,000 Pa·s.

In relation to the structurant, it has been found that the listed zero-shear viscosity ranges provide for the desired structuring, and therefore the desired thickening of the oil using the structurant.

The concentrates of the present invention, have a decrease in viscosity when not under shear (zero-shear) between 24 hours and 14 days of no more than 30%, preferably no more than 20%, most preferably no more than 15%.

The concentrates of the present invention, have a decrease in viscosity under low shear between 24 hours and 14 days of no more than 30%, preferably no more than 20%, most preferably no more than 15%.

The concentrates of the present invention, have a suspensibility of no greater than 2 ml for both creaming and sedimentation according to CIPAC MT 180.

Agrochemically active compounds require a formulation which allows the active compounds to be taken up by the plant/the target organisms. When concentrates (solid or liquid) are used as the source of active agrochemical and/or adjuvant, the concentrates will typically be diluted to form end-use formulations, typically spray formulations. The dilution may be with water at from 1 to 10,000, particularly 10 to 1,000, times the total weight of the concentrate to form the spray formulation.

Said concentrates may be diluted for use resulting in a dilute composition resulting in an agrochemical active concentration of about 0.5 wt. % to about 1 wt. %. In said dilute composition (for example, a spray formulation, where a spray application rate may be from 10 to 500 $l·ha^{-1}$) the agrochemical active concentration may be in the range from about 0.001 wt. % to about 1 wt. % of the total formulation as sprayed.

Spray formulations are aqueous agrochemical formulations including all the components which it is desired to apply to the plants or their environment. Spray formulations can be made up by simple dilution of concentrates containing desired components (other than water), or by mixing of the individual components, or a combination of diluting a concentrate and adding further individual components or mixtures of components. Typically such end use mixing is carried out in the tank from which the formulation is sprayed, or alternatively in a holding tank for filling the spray tank. Such mixing and mixtures are typically termed tank mixing and tank mixtures.

Where the agrochemical active is present in the aqueous end use formulation as solid particles, most usually it will be present as particles mainly of active agrochemical. However, if desired, the active agrochemical can be supported on a solid carrier e.g. silica or diatomaceous earth, which can be a solid support, filler or diluent material.

The spray formulations will typically have a pH within the range from moderately acidic (e.g. about 3) to moderately alkaline (e.g. about 10), and particular near neutral (e.g. about 5 to 8). More concentrated formulations will have similar degrees of acidity/alkalinity, but as they may be largely non-aqueous, pH is not necessarily an appropriate measure of this.

The agrochemical formulation may include solvents (other than water) such as monopropylene glycol, oils which can be vegetable or mineral oils such as spray oils. Such solvents may be included as a solvent for the surfactant adjuvant, and/or as a humectant, e.g. especially propylene glycol. When used such solvents will typically be included in an amount of from 5 wt. % to 500 wt. %, desirably 10 wt. % to 100 wt. %, by weight of the surfactant adjuvant. Such combinations can also include salts such as ammonium chloride and/or sodium benzoate, and/or urea especially as gel inhibition aids.

Surfactants are commonly included in OD formulations, in particular but not exclusively to (a) aid dispersion of the active in the oil; and (b) incorporate emulsifier to promote ready emulsification of the oil flowable on dilution with water prior to spraying. For both purposes, it is desirable to use surfactants that are either soluble or dispersible in the oil and thus the choice of surfactant in any particular case will depend on the oil used.

Surfactants which may be included to aid dispersion of the active in the oil include polymeric dispersants such as those available from Croda, including polyhydroxyester, particularly poly(hydroxystearic) acid such as Atlox LP-1; ABA polyhydroxyester-PEG-polyhydroxyester copolymers such as Hypermer B-246 and Zephrym PD 2206; polyamine modified polyesters such as Atlox LP-6; and alkyd type copolyesters such as Atlox 4914. With such dispersant surfactants, the amount included in an oil flowable formulation will typically be from 1 wt. % to 25 wt. %, more usually from 2.5 wt. % to 15 wt. %, and desirably from 2.5 wt. % to 12.5 wt. % of the total formulation.

Surfactants which may be included as emulsifiers to promote ready emulsification of the oil flowable on dilution with water prior to spraying include anionic surfactants particularly sulphonated hydrocarbon surfactants e.g. alkylbenzene sulphonates, particularly as salts such as alkaline earth metal e.g. calcium, salts particularly calcium didodecylbenzene sulphonate; and non-ionic surfactants including block copolymer polyalkoxylates such as those sold under the tradenames Synperonic PE and Atlas G-5000; alkoxylated, particularly ethoxylated fatty alcohols such as those sold under the tradenames Synperonic A and Synperonic 13; sorbitan esters such as those sold under the tradename Span; ethoxylated sorbitan esters such as those sold under the tradename Tween; and ethoxylated sorbitol esters such as POE (40) sorbitol septaoleate such as that sold under the tradename Arlatone T(V) or POE (50) sorbitol hexaoleate such as that sold under the tradename Atlas G-1096 both from Croda. With such emulsifier surfactants, the amount included in an oil flowable formulation will typically be from 1 wt. % to 25 wt. %, more usually from 2.5 wt. % to 15 wt. %, and desirably from 2.5 wt. % to 12.5 wt. % of the oil used in total formulation.

Typically the total surfactant loading including dispersants for the suspended actives and emulsifiers for the oil will be from 5 wt. % to 35 wt. %, more usually from 10 wt. % to 20 wt. %, and desirably from 5 wt. % to 15 wt. % of the total formulation.

Different types of oils may require different types of surfactant. Thus, for agrochemical formulations based on oils as follows (illustrated with surfactants commercially available from Croda):

triglyceride oils—combinations of non-ionic surfactants such as esters of ethoxylated polyols e.g. POE (50) sorbitol hexaoleate (Atlas G-1096) or POE (40) sorbitol septaoleate (Arlatone T(V)), alkyd type copolyesters (Atlox 4914) and anionic surfactants such as alkyl aryl sulphonates usually in salt form such as amine e.g. the isopropylamine alkyl aryl sulphonate Zephrim 330B; commonly in further in combination with polymeric surfactants such as Atlox polymeric surfactants, or block copolymeric alkoxylates such as Atlas G-5000;

methylated oils—typically use combinations of anionic surfactants such as alkyl aryl sulphonates usually in salt form such as alkali or alkali earth metal salts e.g. the calcium alkyl aryl sulphonate Atlox 4838B (dissolved in ethylhexanol), in combination with a non ionic surfactant such as a fatty alcohol ethoxylates such as $C_{12-15}$3 to 20 ethoxylates e.g. Synperonic series especially A3, A7, A11, A20, or block copolymeric alkoxylates such as Atlas G-5000;

ester oils such as lower alkyl, particularly methyl esters e.g. methyl oleate, —typically use combinations of non-ionic surfactants, particularly alcohol ethoxylates usually having relatively high HLB values e.g. Synperonic A20, and block copolymeric alkoxylates such as Atlas G-5000 (A-B block) and Synperonic PE105 (A-B-A block), with anionic surfactants such as alkyl aryl sulphonates, particularly linear alkyl benzene sulphonates such as dodecyl benzene sulphonate, especially as calcium salts; mineral oils—combinations of non-ionic surfactants, particularly polyol esters such as sorbitan esters e.g. Span series sorbitan esters particularly Span 80 sorbitan oleate, ethoxylated sorbitan esters e.g. Tween series ethoxylated sorbitan esters particularly Tween 85 POE 20 sorbitan trioleate, and alkyl alkyl sulphonates such as Zephrim 330B;

isoparaffinic oils—esters of ethoxylated polyols e.g. POE (40) sorbitol hexaoleate such as Atlas G-1086 or POE (50) sorbitol hexaoleate such as Atlas G-1096, or block copolymeric alkoxylates such as Atlas G-5000, usually in combination with anionic surfactants such as alkyl aryl sulphonates e.g. Atlox 4838B.

aromatic base oils—typically use combinations of non-ionic surfactants, particularly alcohol ethoxylates usually having relatively high HLB values e.g. Synperonic A20, and block copolymeric alkoxylates such as Atlas G-5000 with anionic surfactants such as alkyl aryl sulphonates, particularly linear alkyl benzene sulphonates such as dodecyl benzene sulphonate, especially as calcium salts.

The surfactants used may influence the performance of the structurant, and some improve it. Thus, for example in formulations based on paraffinic oils such as Puccini 19P from Q8, we have found that inclusion of a surfactant combination such as a sorbitan ester (Span 80 sorbitan oleate), an ethoxylated sorbitan ester (Tween 85 POE 20 sorbitan trioleate) and an aryl alkyl sulphonate (Zephrim 330B) seems to improve the compatibility of the structurant with the oil formulation and improves the structuring behaviour as compared with the absence of the surfactants. In general, the ability of the structurant to provide structuring in oil based formulations seems to be broadly independent of the exact chemical nature of the surfactants used. In other words the formulations of the invention are robust to the presence of and variation of surfactants.

The concentrate and/or agrochemical formulation may also include other components as desired. These other components may be selected from those including:

binders, particularly binders which are readily water soluble to give low viscosity solutions at high binder concentrations, such as polyvinylpyrrolidone; polyvinyl alcohol; carboxymethyl cellulose; gum arabic; sugars e.g. sucrose or sorbitol; starch; ethylene-vinyl acetate copolymers, sucrose and alginates, diluents, absorbents or carriers such as carbon black; talc; diatomaceous earth; kaolin; aluminium, calcium or magnesium stearate; sodium tripolyphosphate; sodium tetraborate; sodium sulphate; sodium, aluminium and mixed sodium-aluminium silicates; and sodium benzoate, disintegration agents, such as surfactants, materials that swell in water, for example carboxy methylcellulose, collodion, polyvinylpyrrolidone and microcrystalline cellulose swelling agents; salts such as sodium or potassium acetate, sodium carbonate, bicarbonate or sesquicarbonate, ammonium sulphate and dipotassium hydrogen phosphate;

wetting agents such as alcohol ethoxylate and alcohol ethoxylate/propoxylate wetting agents;

dispersants such as sulphonated naphthalene formaldehyde condensates and acrylic copolymers such as the comb copolymer having capped polyethylene glycol side chains on a polyacrylic backbone;

emulsifiers such as alcohol ethoxylates, ABA block co polymers, or castor oil ethoxylates;

antifoam agents, e.g. polysiloxane antifoam agents, typically in amounts of 0.005 wt. % to 10 wt. % of the formulation;

viscosity modifiers such as commercially available water soluble or miscible gums, e.g. xanthan gums, and/or cellulosics, e.g. carboxy-methyl, ethyl or propylcellulose; and/or preservatives and/or anti-microbials such as organic acids, or their esters or salts such as ascorbic e.g. ascorbyl palmitate, sorbic e.g. potassium sorbate, benzoic e.g. benzoic acid and methyl and propyl 4-hydroxybenzoate, propionic e.g. sodium propionate, phenol e.g. sodium 2-phenylphenate; 1,2-benzisothiazolin-3-one; or formaldehyde as such or as paraformaldehyde; or inorganic materials such as sulphurous acid and its salts, typically in amounts of 0.01 wt. % to 1 wt. % of the formulation.

The invention further includes a method of treating plants using agrochemical formulations including at least one agrochemical active, surfactant adjuvant, and structurant. These may formed by dilution of the concentrate of the first aspect.

Accordingly the invention further includes methods of use including:

a method of killing or inhibiting vegetation or pests by applying to the vegetation, or the immediate environment of the vegetation e.g. the soil around the vegetation, a spray formulation including at least one dispersed phase agrochemical, oil, and the structurant of the first aspect.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 25° C.), unless otherwise stated herein, or unless otherwise stated in the referenced test methods and procedures.

The following test methods were used to determine performance of the adjuvant compositions.

Stability—The stability of all the formulations was assessed after the stated time period at room temperature (RT) and 54° C. The samples were visually assessed to measure any sedimentation/creaming that may have occurred.

Viscosity—Samples were tested on a TA Instruments DHR-3 rheometer. The rheometer was used to assess their stability over the stated time period. This was done measuring the viscosity profiles and the changes in the samples structure and behaviour over the stated time period. The flow test measured the sample viscosity over a range of torques (force) and was used to look at the storage viscosity and application viscosity of a formulation. As the samples were shear thinning (viscosity decreases with increasing torque), the range over which they shear thin provides information on how homogeneous the samples structure was.

Suspensibility (CIPAC MT 180)—Sample was diluted in 342 ppm hard water with 5 ml of concentrate and 95 ml of water. 40 ml of 342 ppm $Ca^{2+}$ water was placed in 100 ml stoppered measuring cylinder. 5 ml of the formulation was added and topped up to 100 ml mark with 342 $Ca^{2+}$ ppm water (mimicking a 20 fold dilution upon application). The sample was inverted 30 times and left to stand for 30 minutes.

Example Formulations with Neat Oils

Various structurants of the present invention were added to neat oils to show structuring ability. The structurant was heated and mixed in to the oil and stirred at about 500 rpm until a homogenous liquid was obtained, with the temperature required depended on the structurant used. Samples were then left to cool.

The structurants tested are listed in Table 1.

TABLE 1

| | Structurants |
|---|---|
| Example | Chemical Name |
| S1 | Ester terminated polyesteramide formed from $C_{36}$ dimer acid, ethylenediamine, neopentyl glycol, and stearyl alcohol |
| S2 | Amide terminated polyamides formed from $C_{36}$ dimer acid, ethylenediamine, and di-$C_{14-18}$ alkyl amine |
| S3 | Amide terminated polyamides formed from $C_{36}$ dimer acid, ethylenediamine, and di-$C_{14-18}$ alkyl amine |
| S4 | Ester terminated polyamide formed from $C_{36}$ dimer acid, ethylenediamine, and stearyl alcohol |

Visual observations of the structurants with neats oils were made under the incorporation conditions shown in Table 2.

TABLE 2

| | Incorporation at 3 wt. % | | | |
|---|---|---|---|---|
| | Sturcturant Used | | | |
| Oil | S1 | S2 | S3 | S4 |
| Sunflower oil | Homogeneous gel, pourable | Homogeneous gel, pourable | Homogeneous gel, pourable | Homogeneous gel, pourable |
| MSO | Homogenous gel pourable | Homogenous gel pourable | Homogenous gel pourable | Homogenous gel pourable |
| SunAG oil | Homogenous gel pourable | Homogenous gel pourable | Homogenous gel pourable | Homogenous gel pourable |
| Rapeseed oil | Homogenous gel pourable | Homogenous gel pourable | Homogenous gel pourable | Homogenous gel pourable |

The results in Table 2 show that the structurants provide stable structured compositions with a variety of oils.

Rheology

The storage viscosity was determined to show the viscosity of the neat oils and 3 wt. % structurant when under zero shear. The storage viscosity was measured by taking a point from the samples flow curve (viscosity profile) at the low torque end. The results are shown in Table 3.

TABLE 3

Storage viscosity under zero shear (units are Pa · s)

| Oil | Sturcturant Used | | | |
|---|---|---|---|---|
|  | S1 | S2 | S3 | S4 |
| Sunflower oil | 6,921 | 8,583 | 8,432 | 5,247 |
| MSO | 19,4472 | 54,651 | 16,201 | 32,308 |
| SunAG oil | 15,245 | 24,862 | 8,955 | 10,648 |
| Rapeseed oil | 23,563 | 12,311 | 18,477 | 12,268 |

The results show that the structurants were able to form thickened oils under conditions of no shear (zero torque).

Structure Recovery

The gelling system was subjected to a high shear and left to rebuild to check that the gelling agents would still gel the oil after shear. This simulates milling which would be typically performed when forming concentrates of this type, and therefore it is important that the structurant can continue to function after such milling. The results are shown in Table 4 using neat rapeseed oil with 3 wt. % of structurant S1.

TABLE 4

Viscosity for structure recovery after shear (units are Pa)

|  | G' initial | G' after shear | G' when recovered* |
|---|---|---|---|
| S1 at 3 wt. % in rapeseed oil | 104.472 | 63.3 | 104.248 |

*Recovered after 18 minutes (1,100 seconds).

The elastic/storage modulus (denoted as G') is the measure of a sample's elastic behaviour, i.e. a measure of the elastic response of a material). The results show that the structured oil thinned under shear as desired, and then recovered completely back to the original thickness after a short time. This shows that the structured oil can be processed in a mill as it shear thins, but also that the structure recovers after being milled.

Concentrate Examples with Active

A number of active containing concentrates were made up using structurant S1, and a concentrate was made using clay which is an existing compounds used for structuring. The clay was organically modified Bentonite clay (Disteardimonium Hectorite). The concentrates are detailed in Table 5.

TABLE 5

Concentrates formed

| Component | Function | Concentrate (amount in wt. %) | | |
|---|---|---|---|---|
|  |  | C1 | C2 | A1 |
| Zinc oxide | Active | 44.4 | — | — |
| Copper oxychloride | Active | — | 44.08 | 44.58 |
| Atlox LP1 | Aqueous dispersant | 4.4 | — | — |
| Atlox 4915 | Non aqueous dispersant | 4.4 | — | — |
| Metasperse 550S | Aqueous dispersant | — | 0.81 | 0.81 |
| Zephrym PD-2206 | Non-aqueous dispersant | — | 0.81 | 0.81 |

TABLE 5-continued

Concentrates formed

| Component | Function | Concentrate (amount in wt. %) | | |
|---|---|---|---|---|
|  |  | C1 | C2 | A1 |
| Atlas G1086 | Emulsifier | 7.3 | 7.2 | 7.2 |
| S1 | Structurant | 2.0 | 3.5 | — |
| Clay | Structurant | — | — | 3.0 |
| Methylated seed oil | Continuous phase | 37.5 | — | — |
| Rapeseed oil | Continuous phase | — | 43.6 | 43.6 |

The stability with regard to separation for concentrates C1, C2, and A1 was tested and assessed visually at room temperature (RT) and at raised temperature after 24 hours and 14 days according to method CIPAC MT46.1.3. Table 6 shows the visual observation results.

TABLE 6

Visual separation results

|  | 24 hours | | 14 days | |
|---|---|---|---|---|
| Concentrate | RT | 54° C. | RT | 54° C. |
| C1 | NS | NS | NS | 1% St |
| C2 | NS | NS | 1% St | 9% St |
| A1 | NS | Tt | Tt | Br |

NS—signifies no separation
St—signifies separation at top (>1 and <20%) oil
Br—broken
Tt—trace separation top i.e. <1%
RT—room temperature The C1 and C2 concentrates did not appear to be visually impacted either at room temperature or at elevated temperature over the 24 hour period. During the longer 14 day period only negligible separation was observed. The clay based concentrate A1 showed significant separation, and completely separated during the 14 day period.

It should be noted that testing at elevated temperature was performed as it is generally understood to represent an accelerated way of assessing room temperature properties over time. For example, a concentrate kept at 54° C. for 14 days is understood to provide similar results compared to keeping a concentrate at room temperature for two years.

Dispersibility was also determined for the concentrates C1, C2, and A1 according to method CIPAC MT180. The results are shown in Table 7.

TABLE 7

Dispersibility results

| Label | 30 minutes | 2 hours |
|---|---|---|
| C1 | No creaming <1.0 ml sedimentations | No creaming 2.0 ml sedimentation |
| C2 | 0.5 ml cream 0.5 ml sediment | 0.5 ml cream 0.5 ml sediment |
| A1 | 5.0 ml cream, 1.0 ml sediment | 5.0 ml cream, 1.5 ml sediment |

Both concentrates C1 and C2 show little if any sedimentation or creaming over 30 minutes or 2 hours. Comparative concentrate A1 using clay as a structurant shows significant and unacceptable creaming and sedimentation over 30 minutes and 2 hours.

The concentrates were subjected to differing levels of shear to assess viscosity performance.

TABLE 8

| | Viscosity performance under shear (units are Pa · s) | | | | | |
|---|---|---|---|---|---|---|
| | Viscosity after 24 hours at RT | | | Viscosity after 14 days at RT | | |
| Label | 0 μNm Torque | 5 μNm Torque | 200 μNm Torque | 0 μNm Torque | 5 μNm Torque | 200 μNm Torque |
| C1 | 14,4551 | 14,1201 | 9.541 | 13,8257 | 13,5292 | 3.254 |
| C2 | 58,696.7 | 63,766 | 26.614 | 39,854.9 | 36,875.4 | 19.568 |
| A1 | 49,021.1 | 46,217.8 | 224.762 | Unstable | Unstable | Unstable |

The results show that both concentrates C1 and C2 structure to a desired level under zero shear. Under shear of 200 μNm the concentrates shear thin as would be required during milling to a suitable level. This performance is still retained when the concentrates are left stored for 14 days at room temperature. This is advantageous over existing structurants which don't typically shear thin sufficiently, and therefore cause processing/milling problems as they are too thick.

The concentrate A1 does not shear thin sufficiently under shear of 200 μNm, and therefore would cause processing/milling problems as it would be too thick. Additionally, on storing for 14 days the concentrate A1 became unstable.

As a result of the tests it can be seen that the structurants of the present invention were shown to produce stable structured concentrates with a number of different oils covering.

It is to be understood that the invention is not to be limited to the details of the above embodiments, which are described by way of example only. Many variations are possible.

The invention claimed is:

1. An agrochemical concentrate comprising;
   i) an oil system comprising an oil and at least one structurant, said structurant being a polyamide formed from a dicarboxylic acid comprised from a dimer acid compound, and one or more diamine compounds;
   ii) at least one agrochemical active and/or nutrient dispersed in said oil system.

2. The concentrate according to claim 1, wherein the dimer acid is derived from the dimerisation products of $C_{10}$ to $C_{30}$ fatty acids.

3. The concentrate according to claim 1, wherein the dimer acid is derived from the dimerisation product of oleic acid, linoleic acid, linolenic acid, palmitoleic acid, or elaidic acid.

4. The concentrate according to claim 1, wherein the diamine is represented by the formula $H(R^3)N-R^2-N(R^4)H$, where $R^2$ is a hydrocarbon group having 2 to 36 carbon atoms, and where $R^3$ and $R^4$ each represent hydrogen.

5. The concentrate according to claim 4, wherein the diamine is selected from ethylenediamine (EDA), 1,2-diaminopropane, 1,3-diaminopropane, 1,4-diaminobutane, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, all isomers of diaminophenanthrene, 4,4'-methylenebis(cyclohexylamine), 2,7-diaminofluorene, 1,2, 1,3, and/or 1,4 isomers of phenylene diamine, adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, all isomers of diaminonaphthalene, and 4-amino-2,2,6,6-tetramethylpiperidine.

6. The concentrate according to claim 1, wherein the structurant is formed with a polyol to form polyesteramide.

7. The concentrate according to claim 6, wherein the polyol is a $C_2$ to $C_{20}$ polyol having in the range from 2 to 9 hydroxyl groups.

8. The concentrate according to claim 6, wherein the polyol is selected from ethylene glycol, propylene glycol, butylene glycol, glycerol, trimethylolpropane, pentaerythritol, neopentyl glycol, tris (hydroxylmethyl) methanol, dipentaerythritol, and tripentaerythritol.

9. The concentrate according to claim 1, wherein the structurant is an ester terminated polyamide.

10. The concentrate according to claim 1, wherein the structurant is an amide terminated polyamide.

11. The concentrate according to claim 1, wherein the structurant is be selected from:
    ester terminated polyamides formed from $C_{36}$ dimer acid, ethylenediamine, and behenyl alcohol or stearyl alcohol;
    amide terminated polyamides formed from $C_{36}$ dimer acid, ethylenediamine, and ditetradecyl amine or dipentadecyl amine or dicetyl amine or diheptadecyl amine or distearyl amine; and
    ester terminated polyesteramides formed from $C_{36}$ dimer acid, ethylenediamine, neopentyl glycol, and behenyl alcohol or stearyl alcohol.

12. The concentrate according to claim 1, wherein the amount of structurant present in the concentrate is in the range from 0.5 wt. % to 10.0 wt. %.

13. The concentrate according to claim 1, wherein the oil has a Hansen and Beerbower solubility $\delta'$ parameter (HBSP) value ranging from 12 to 22.

14. A method of preparing a concentrate according to claim 1, said method comprising mixing;
    at least one structurant, said structurant being apolyamide formed from a dicarboxylic acid comprised from a dimer acid compound, and one or more diamine compounds, and an oil to form an oil system; and
    at least one agrochemical active and/or nutrient.

15. An agrochemical formulation formed by dilution of the concentrate according to claim 1.

16. A method of treating vegetation to control pests, the method comprising applying an agrochemical formulation according to claim 15, either to said vegetation or to the immediate environment of said vegetation.

* * * * *